United States Patent
Nygaard et al.

(10) Patent No.: US 8,896,844 B2
(45) Date of Patent: Nov. 25, 2014

(54) HIGH-SPEED, 3-D METHOD AND SYSTEM FOR OPTICALLY MEASURING A GEOMETRIC DIMENSION OF MANUFACTURED PARTS

(71) Applicant: GII Acquisition, LLC, Davisburg, MI (US)

(72) Inventors: Michael G. Nygaard, Fenton, MI (US); Kyle M. Harmer, Swartz Creek, MI (US); Nathan Andrew-Paul Kujacznski, Flint, MI (US); James W. St. Onge, Bloomfield Hills, MI (US)

(73) Assignee: GII Acquisition, LLC, Davisburg, MI (US)

(*) Notice: Subject to any disclaimer, the term of this patent is extended or adjusted under 35 U.S.C. 154(b) by 0 days.

(21) Appl. No.: 13/714,999

(22) Filed: Dec. 14, 2012

(65) Prior Publication Data

US 2014/0168661 A1    Jun. 19, 2014

(51) Int. Cl.
*G01B 11/24*    (2006.01)
*G01B 11/02*    (2006.01)

(52) U.S. Cl.
CPC ............... *G01B 11/24* (2013.01); *G01B 11/02* (2013.01)
USPC ........................................................ 356/601

(58) Field of Classification Search
CPC ...... G01B 11/24; G01B 11/25; G01B 11/306; G01B 11/245; G06T 7/0057
USPC ................. 345/419; 356/237.2, 601; 702/185
See application file for complete search history.

(56) References Cited

U.S. PATENT DOCUMENTS

| | | | |
|---|---|---|---|
| 4,831,251 A | 5/1989 | Hanna | |
| 4,923,066 A | 5/1990 | Ophir et al. | |
| 5,025,706 A * | 6/1991 | Markle | 86/37 |
| 5,383,021 A | 1/1995 | Hanna | |
| 5,568,263 A | 10/1996 | Hanna | |
| 5,661,667 A * | 8/1997 | Rueb et al. | 702/95 |
| 6,252,661 B1 | 6/2001 | Hanna | |
| 6,285,034 B1 | 9/2001 | Hanna et al. | |

(Continued)

FOREIGN PATENT DOCUMENTS

WO    2005022076 A2    3/2005

OTHER PUBLICATIONS

Military Standard Visual Inspection Standards for Small Arms Ammunition Through Caliber .50; http://www.assistdocs.com; downloaded: Nov. 3, 2005T20.42Z.

(Continued)

*Primary Examiner* — Tarifur Chowdhury
*Assistant Examiner* — MD Rahman
(74) *Attorney, Agent, or Firm* — Brooks Kushman P.C.

(57) ABSTRACT

A high-speed, 3-D method and system for optically measuring a geometric dimension of manufactured parts such as cartridge cases are provided. The method includes consecutively transferring the parts so that the parts travel along a path which extends to a vision station at which each part has a predetermined position and orientation for optical measuring. A line of radiation having a predetermined orientation is projected onto spaced apart end surfaces of the part to obtain reflected line segments of radiation from the end surfaces of the part. The reflected line segments of radiation are detected at one or more image planes to obtain electrical signals and the electrical signals are processed to determine the geometric dimension such as primer pocket depth.

20 Claims, 16 Drawing Sheets

(56) References Cited

U.S. PATENT DOCUMENTS

| | | |
|---|---|---|
| 6,313,948 B1 | 11/2001 | Hanna |
| 6,787,724 B2 | 9/2004 | Bennett et al. |
| 6,935,034 B2 * | 8/2005 | Malard et al. ................... 33/286 |
| 6,959,108 B1 | 10/2005 | Bartelt et al. |
| 6,995,837 B1 | 2/2006 | Moir et al. |
| 7,164,783 B2 | 1/2007 | Yang et al. |
| 7,245,759 B2 | 7/2007 | Jones, Jr. et al. |
| 7,403,872 B1 * | 7/2008 | St. Onge et al. .............. 702/185 |
| 7,491,319 B1 | 2/2009 | Yang |
| 7,669,707 B2 | 3/2010 | Kenneway |
| 7,801,692 B2 | 9/2010 | Yang |
| 8,154,683 B2 | 4/2012 | Yoneda et al. |
| 2005/0174567 A1 | 8/2005 | Hanna |
| 2005/0226489 A1 | 10/2005 | Beach et al. |
| 2006/0236792 A1 | 10/2006 | Hanna |
| 2010/0245850 A1 | 9/2010 | Lee et al. |
| 2012/0105429 A1 * | 5/2012 | Nygaard ....................... 345/419 |
| 2012/0268748 A1 | 10/2012 | Walstra |
| 2013/0235371 A1 * | 9/2013 | Nygaard et al. ........... 356/237.2 |

OTHER PUBLICATIONS

International Search Report and Written Opinion; International application No. PCT/US13/73058; date of mailing Jan. 29, 2014.

* cited by examiner

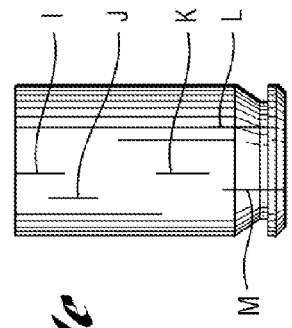
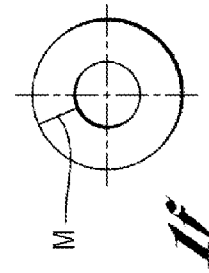
Fig. 1e
Fig. 1f
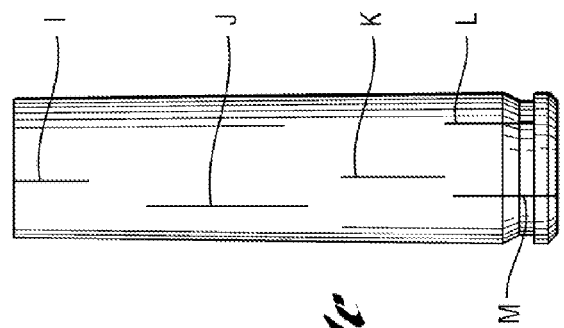
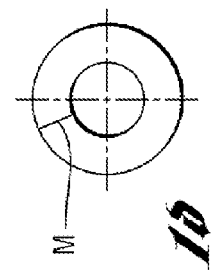
Fig. 1c
Fig. 1d
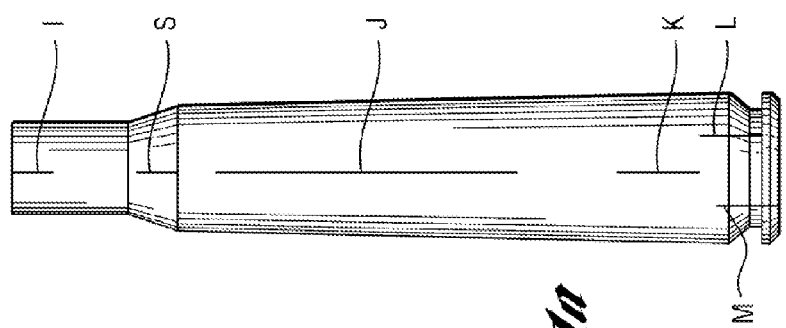
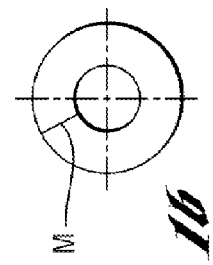
Fig. 1a
Fig. 1b

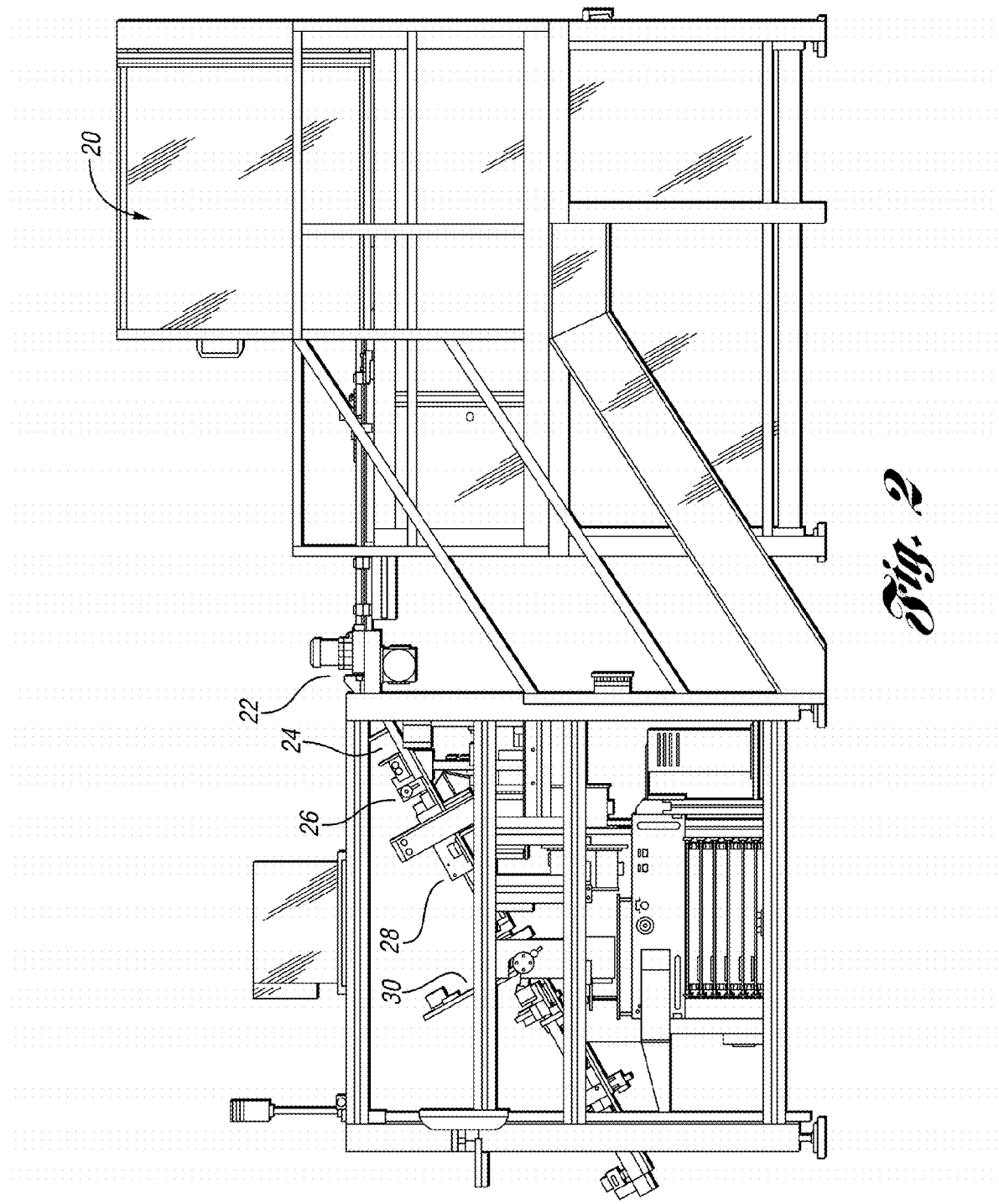

HIGH-SPEED, 3-D METHOD AND SYSTEM FOR OPTICALLY MEASURING A GEOMETRIC DIMENSION OF MANUFACTURED PARTS

CROSS-REFERENCE TO RELATED APPLICATION

This application is related to U.S. patent application entitled "HIGH-SPEED METHOD AND SYSTEM FOR OPTICALLY MEASURING A GEOMETRIC DIMENSION OF A MANUFACTURED PART" filed on the same day as this application.

TECHNICAL FIELD

This invention relates in general to the field of non-contact, optical inspection and measurement of parts and, more particularly, to high-speed, 3-D methods and systems for optically measuring geometric dimension of manufactured parts such as cartridge cases.

Overview

Traditional manual, gauging devices and techniques have been replaced to some extent by automatic inspection methods and systems. However, such automatic inspection methods and systems still have a number of shortcomings associated with them especially when the parts being inspected have apertured exterior and/or interior surfaces that need to be measured.

The inspection of firearm cartridges presents unique challenges. A firearm cartridge includes a case defining an interior volume containing gunpowder, having a rear end defining a central primer pocket receiving a primer, and defining a case mouth at a forward end opposite the rear end.

Inspection of defects on small arms ammunition cartridges and cases is a vital aspect in the manufacturing process, allowing for maintenance of a high level of quality and reliability in the munitions industry. Standards have been developed and applied by manufacturers for many years to assists in classifying various types of defects. Alternatively, a military standard is used such as that introduced in 1958 by the US Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

FIGS. 1a and 1b are side and bottom end schematic views, respectively, of a .50 caliber case. As explained in the above-noted military standard, a case is to be counted as a defective because of a split case if the cartridge case shows a definite separation of the metal entirely through the case wall. A case is to be classified as either a "major" or "critical" defect depending on the location of split. A split in the neck (I), taper (S) or case (J) position shall be counted as a "major" defect when no loss of powder occurs; and as a "critical" defect when loss of powder occurs. A split in the case (K), groove (L) or head (M) position shall be counted as a "critical" defect.

FIGS. 1c and 1d are side and bottom end schematic views, respectively, of a .30 caliber case. As noted above, a case is to be counted as a defective because of a split case if the cartridge case shows a definite separation of the metal entirely through the case wall. A case is to be classified either as a "major" or "critical" defective depending on location of split. A split in the (I) or (J) position shall be counted as a "major" defect when no loss of powder occurs, and as a "critical" defect when loss of powder occurs. A split in the (K), (L) or (M) positions shall be counted as a "critical" defect.

FIGS. 1e and 1f are side and bottom end schematic views, respectively, of a .45 caliber case. Again, as noted above, a case is to be counted as defective because of a split case if the cartridge case shows a definite separation of the metal entirely through the case wall. A case is to be classified either as a "major" or "critical" defective depending on the location of the split. A split in the (I) or (J) position shall be counted as a "major" defect when no loss of powder occurs. A split in the (K), (L) or (M) position shall be counted as a "critical" defect.

U.S. Pat. No. 4,923,066 discloses an automatic visual inspection system for small arms ammunition which sorts visual surface flaws at high speed according to established standards. The system comprises interface apparatus for receiving a supply of ammunition cartridges and providing each cartridge with a predetermined orientation, conveying apparatus for locating each of the cartridges for inspection in at least one inspection station, apparatus for imaging selected areas of each cartridge to provide video surface feature data associated therewith, and apparatus for processing the video surface feature data to detect the presence of a predetermined set of characteristics and provide output signals in accordance therewith, the conveying apparatus being operated to sort each of the inspected cartridges in accordance with the output signals. Since many surface flaws look the same in two dimensions, such as scratches and splits or acid holes and stains, special lighting of the cartridges is used so that discrimination between them can be achieved on the basis of off-specular reflections.

U.S. Pat. No. 7,403,872 discloses a method and system for inspecting manufactured parts, such as cartridges and cartridge cases, at a plurality of inspection stations including a circumference vision station and primer and mouth vision stations.

WO 2005/022076 discloses a plurality of light line generators which generate associated beams of light that intersect a part to be inspected. Each beam of light illuminates at least one side of the part with a line of light occluded by the part, and at least three light responsive sensors provide for generating a signal responsive to an occlusion of a corresponding line of light on a corresponding side of at least one side of the part. Each of the light responsive sensors is responsive to an occlusion at a different azimuthal location.

U.S. Pat. No. 6,959,108 discloses an inspection system wherein workpieces to be inspected are consecutively and automatically launched to pass unsupported through the field of view of a plurality of cameras.

Published U.S. Patent Application 2005/0226489 discloses a machine vision system for automatically identifying and inspecting objects, the system includes composable vision-based recognition modules and a decision algorithm to perform the final determination on object type and quality.

Published U.S. Patent Application 2010/0245850 discloses a system for indirectly measuring a geometric dimension related to an opening in an apertured exterior surface of a part such as an ammunition case based on direct measurements of the part when fixtured at a measurement station. The system includes first and second holding devices for holding the part therebetween in a part-retaining position in which the part is firmly held between the devices at its end surfaces. In one embodiment, a portion of each of the holding devices extends into its respective opening in the part-retaining position. The system also includes a head apparatus which has a plurality of radiation sources for successively directing arrays of planes of radiation at the holding devices and at the part, and a plurality of receiver modules for measuring the amount of radiation present in unobstructed planar portions of the planes to obtain holding device and part signals. The system further includes a movable stage subsystem coupled to the head apparatus for translating the head apparatus. The system still further includes a signal processor for processing the holding device and part signals to obtain data and a data processor for processing the data to obtain the direct measurements. The data processor determines the geometric dimensions related to the openings based on the direct measurements.

Published U.S. Patent Application 2012/0105429 discloses a method and system for high-speed, high-resolution 3-D imaging of manufactured parts of various sizes at an imaging station having a measurement axis. The part has a 3-D end surface and a length, a width and a part axis defined as being central to the part and parallel to its length. The system includes apparatus having a central axis substantially parallel to the measurement axis and a plurality of members having open and closed positions. The members have holding faces which are substantially equidistant from the central axis during movement between the positions to align a part disposed between the holding faces at the station so that the part axis is substantially parallel to the measurement and central axes. The holding faces releasably hold the aligned part in a holding position between the positions. The system further includes an actuator for moving the apparatus so that the end surface moves in a plane substantially perpendicular to the measurement axis. The system still further includes a controller for controlling the actuator to move the end surface along a 2-D trajectory within the plane. The system further includes at least one sensor for emitting a beam of energy along the measurement axis onto the end surface during movement of the end surface along the 2-D trajectory to obtain reflected energy and for sensing at least a portion of the reflected energy to obtain an output. The system still further includes a processor for processing the output to obtain information related to the end surface of the part.

Published U.S. Patent Application 2012/0268748 discloses a method for optically inspecting a part having a length, a diameter and an axis. The method includes supporting the part. The method further includes linearly scanning at least one plane of radiation having a width wider than the diameter of the part onto an exterior side surface of the supported part so that the part occludes the at least one plane of radiation at a plurality of spaced apart locations along the axis to create unobstructed left and right planar portions of the at least one plane of radiation passing by and not blocked by the part. The unobstructed left and right planar portions contain an amount of radiation which is representative of a respective diameter of the part at the plurality of spaced apart locations. The method still further includes measuring the amount of radiation present in the unobstructed left and right planar portions during the step of scanning to obtain measurement signals which represent diameter of the part at each of the plurality of spaced apart locations along the axis. The method further includes processing the measurement signals to obtain input data. The method still further includes forming a virtual representation of an outer profile of the part in a reference frame based on the input data. The method still further includes providing a virtual representation of an inner bore of a physical gauge in the reference frame. The inner bore has a diameter. The method further includes determining an interference position between the part and the gauge using the virtual representations. The interference position is a position along the axis where the bore diameter is substantially equal to the part diameter. The method still further includes calculating a distance along the axis based on the interference position and storing the distance.

U.S. Pat. No. 8,154,683 is assigned to CCS Inc. and discloses an LED ring illuminization device.

Hypercentric lenses provide a converging view of an object, focusing on the top and surrounding sides simultaneously, and are used to eliminate the need for multiple camera and imaging lens setups in machine vision inspection or identification applications. Pericentric or hypercentric lenses suffer from cost, weight and size issues. As a result, linescan products are most commonly used to image parts. Linescan provides high resolution, distortion free images and good control over illumination. However, linescan-based systems also suffer from technical and cost concerns; parts to be inspected must be brightly illuminated and rotated within the camera's field of view (FOV).

Light Works, LLC of Toledo, Ohio markets what it calls Hyper-Eye™ hypercentric lenses which may be used as borescopes.

While the methods and systems described in the above-noted patent documents provide tools for article inspection, there are several important interior, geometric features on parts such as ammunition cartridge cases which are difficult to directly measure in a high-speed fashion using the hardware configurations described in these systems. These features of interest include Mouth Inner Diameter, Primer Pocket Diameter and Primer Pocket Depth when the parts are cartridge cases.

SUMMARY OF EXAMPLE EMBODIMENTS

An object of at least one embodiment of the present invention is to provide a high-speed, 3-D method and system for optically measuring a geometric dimension of manufactured parts such as cartridge cases without the need for part rotation thereby providing a compact, cost-effective and simpler solution to the measurement task.

In carrying out the above object and other objects of at least one embodiment of the present invention, a high-speed, 3-D method of optically measuring a geometric dimension of manufactured parts is provided. Each of the parts has an exterior end surface and an interior end surface at a first end of the part, a length and a width. Each of the parts has a part-holding pocket extending between the end surfaces. The method includes consecutively transferring the parts so that the parts travel along a path which extends to a vision station at which each part has a predetermined position and orientation for optical measuring. The method also includes projecting a line of radiation having a predetermined orientation onto the end surfaces to obtain reflected line segments of radiation from the end surfaces of the part. The method further includes detecting the reflected line segments of radiation at one or more image planes to obtain electrical signals and processing the electrical signals to determine the geometric dimension.

The part may include a cartridge case having a mouth end and a primer end. The end surfaces may be located at the primer end wherein the pocket is a primer pocket.

The end surfaces may be substantially parallel to each other wherein the geometric dimension is primer depth.

The method may further include providing an inclined track to support the part along the path and allowing the part to fall freely onto the inclined track so that the part slides down the track by the force of gravity.

Each part may have a part axis defined as being central to the part and parallel to its length.

The method may further include determining whether the primer depth is within a range of acceptable values.

The method may further include generating a signal based on the determination.

The method may further include coordinating the measuring of the part at the vision station with the transfer of the part to and from the vision station to control movement of the part and the measuring of the part.

The line of radiation may be a line of laser radiation.

The reflected line segments of radiation may be detected in a pair of image planes.

Further, in carrying out the above object and other objects of at least one embodiment of the present invention, a high-speed, 3-D system for optically measuring a geometric dimension of manufactured parts is provided. Each of the parts has an exterior end surface and an interior end surface at a first end of the part, a length and a width. Each of the parts has a part-holding pocket extending between the end surfaces. The system includes a part transfer subsystem including a transfer mechanism adapted to consecutively transfer the parts so that the parts travel along a path which extends to a vision station at which each of the parts has a predetermined position and orientation for optical measuring and to transfer each part after measuring at the vision station so that the measured parts travel along the path which extends from the vision station. The system also includes a projector to project a line of radiation having a predetermined orientation onto the end surfaces to obtain reflected line segments of radiation from the end surfaces. The system further includes at least one lens and detector assembly to form optical images of the reflected line segments of radiation and to detect the optical images to obtain electrical signals. The system finally includes a processor to process the electrical signals to determine the geometric dimension.

The part may include a cartridge case having a mouth end and a primer end, wherein the end surface is located at the primer end and the pocket is a primer pocket.

The end surfaces may be substantially parallel to each other wherein the geometric dimension is primer depth.

The system may include a pair of lens and detector assemblies disposed on opposite sides of the path to form the optical images of the reflected line segments of radiation and to detect the optical images to obtain the electrical signals.

Each part may have a part axis defined as being central to the part and parallel to its length.

Each detector may include an image sensor having an image plane to detect the optical images.

The transfer mechanism may include an inclined track to support the part as the part slides down the track by the force of gravity along the path.

The projector may include a line-generating laser disposed above the path.

The laser may generate a visible vertical line of laser radiation.

The system may further include a computer to determine whether the depth is within a range of acceptable values and to generate a signal based on the determination.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

BRIEF DESCRIPTION OF THE DRAWINGS

FIGS. 1a and 1b are side and bottom schematic views, respectively, of a .50 caliber cartridge case;

FIGS. 1c and 1d are side and bottom schematic views, respectively, of a .30 caliber cartridge case;

FIGS. 1e and 1f are side and bottom schematic views, respectively, of a .45 caliber cartridge case;

FIG. 2 is a side schematic view of a system for inspecting manufactured parts and sorting the inspected parts, the system including a feeder subsystem, a part transfer subsystem and an inspection machine subsystem;

DETAILED DESCRIPTION

Figure 3:
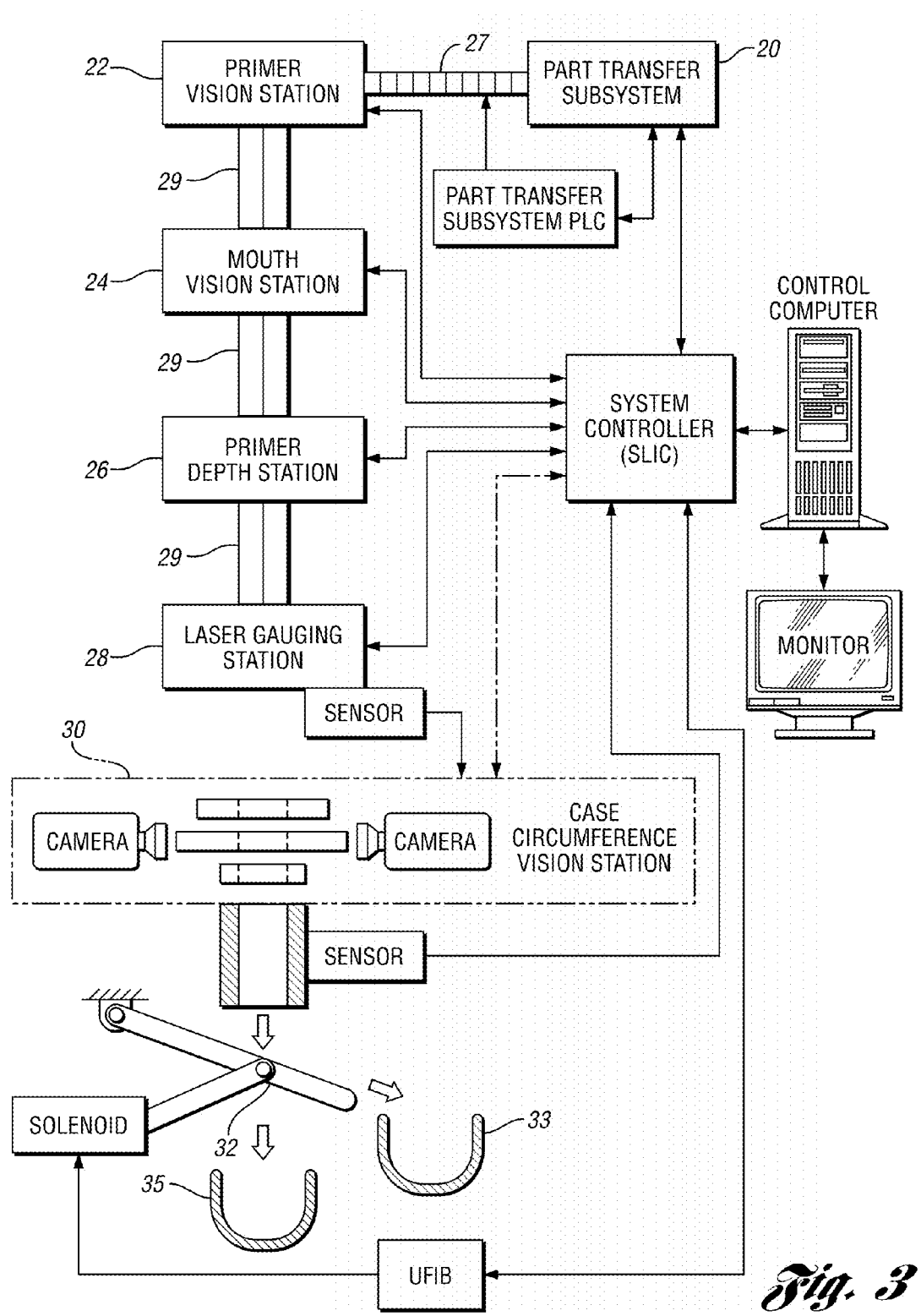
FIG. 3 is a schematic view illustrating various inspection stations and part conveying mechanisms and their control to inspect and sort the inspected parts.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In general, one embodiment of the method and system of the present invention inspects and measures at least one geometric dimension of manufactured parts such as cartridges and cartridge cases illustrated in FIGS. 1a-1f. The parts are typically sorted after inspection and measurement. In general, each of the parts has an exterior end surface, a length, a width, and a part axis defined as being central to the part and parallel to its length. Each of the parts has a part-holding pocket extending from the exterior end surface along the part axis to an interior end surface at primer end of the cartridge case. The system is a complete system designed for the inspection of small and medium caliber ammunition. However, the system is also suitable for other small, mass-produced manufactured parts where the accurate measurement of geometric dimensions of the part are of concern. The subsystems which may be used for part handling and delivery may vary widely from application to application depending on part size and shape as well as what inspections are being conducted. The subsystems ultimately chosen for part handling and delivery have little bearing, however, on the nature of the subsystems conducting the various inspections and measurements, including optical inspections and measurements.

Referring now to FIG. 2, in general, the system accepts parts from an infeed hopper of a part transfer subsystem, generally included at 20, at one end and automatically feeds, orients and conveys them through a number of inspecting or measuring stations as illustrated at 22, 24, 26, 28 and 30 in FIG. 2. The system typically includes a primer vision station 22, a mouth vision station 24, a primer depth station 26, a laser gauging station 28 and a case circumference vision station 30.

Figure 6:
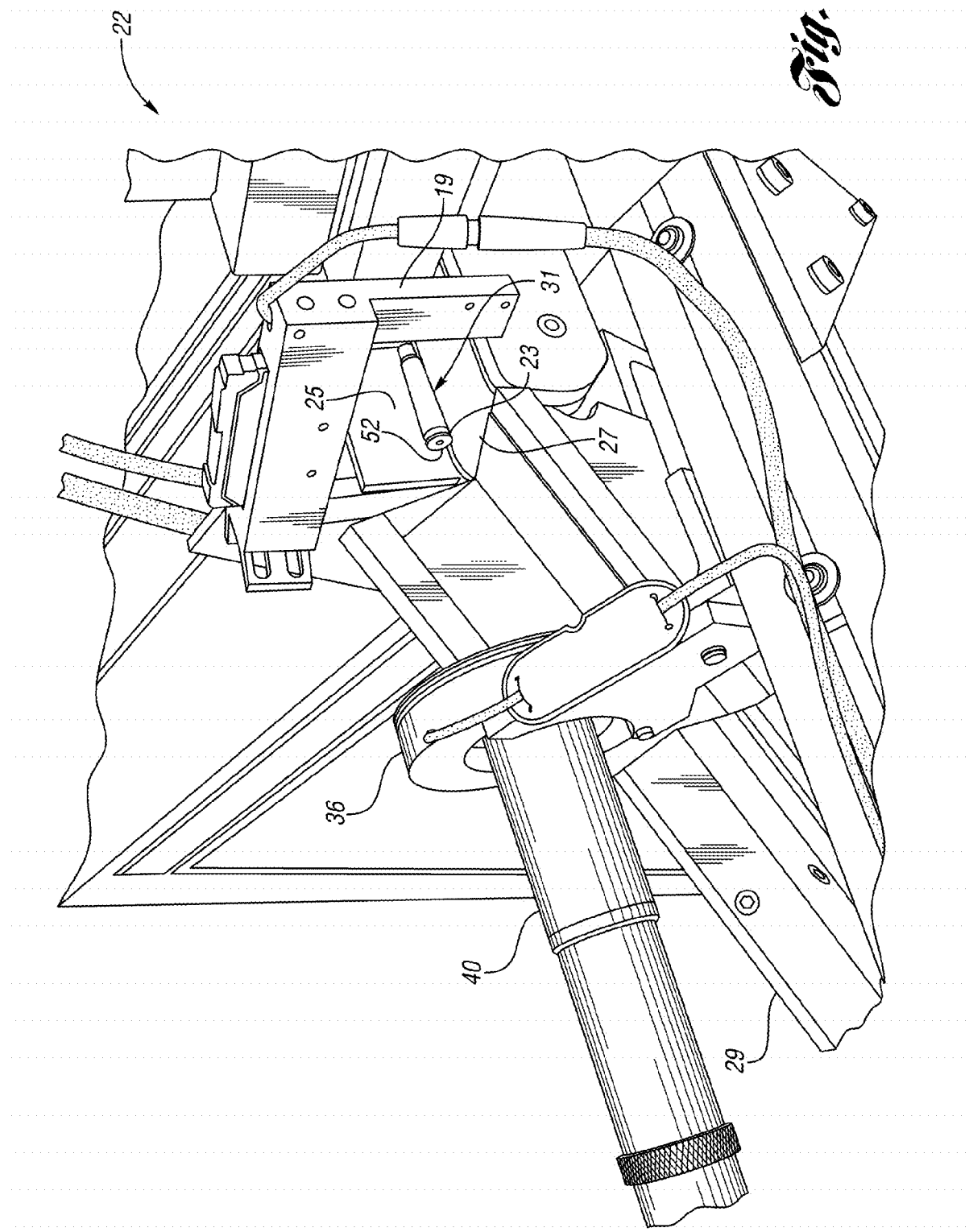
FIG. 6 is a perspective schematic view, partially broken away, of the hardware located at the primer vision station of FIG. 4.
Figure 7:
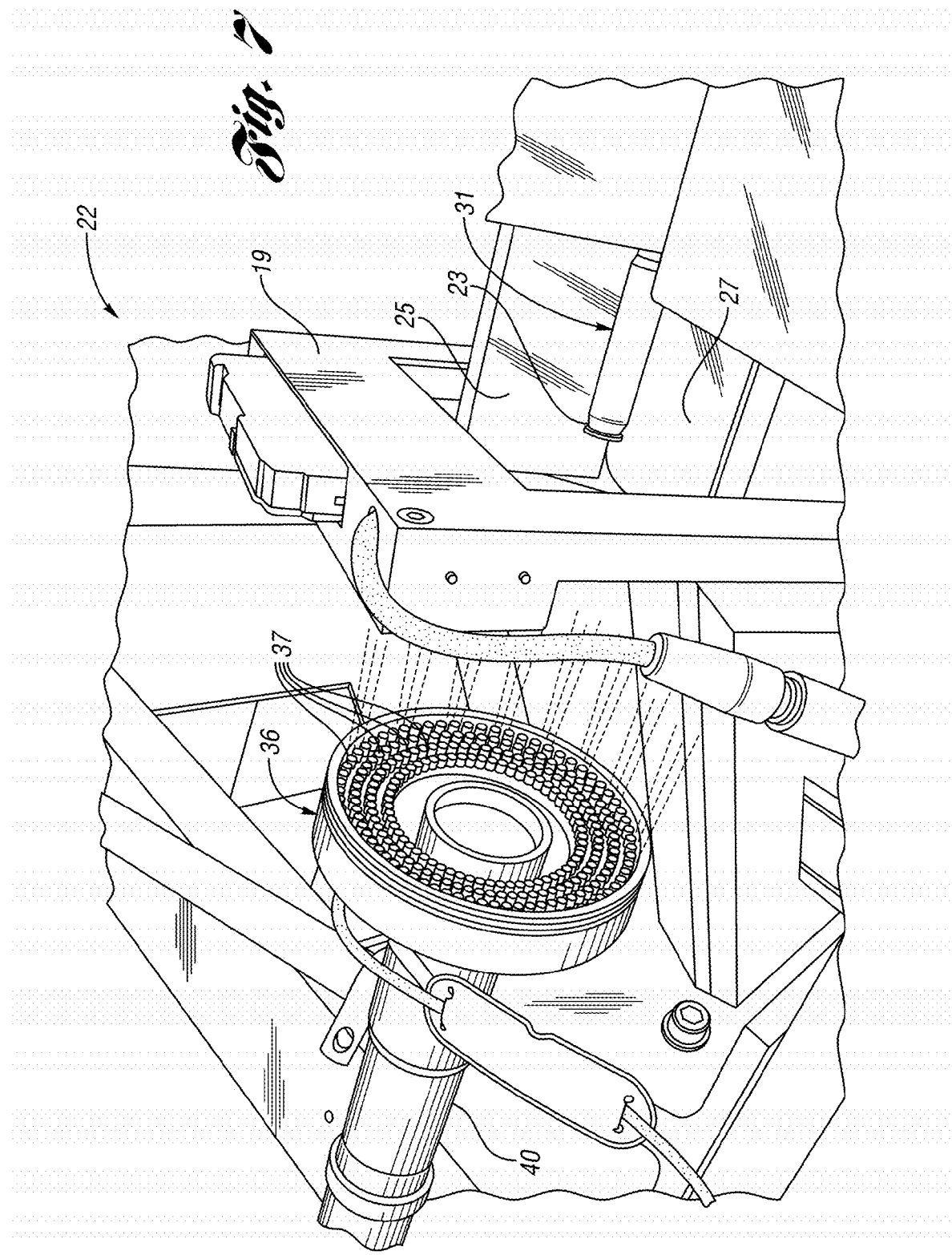
FIG. 7 is a view, similar to the view of FIG. 6, but at a different angle.
Figure 8:
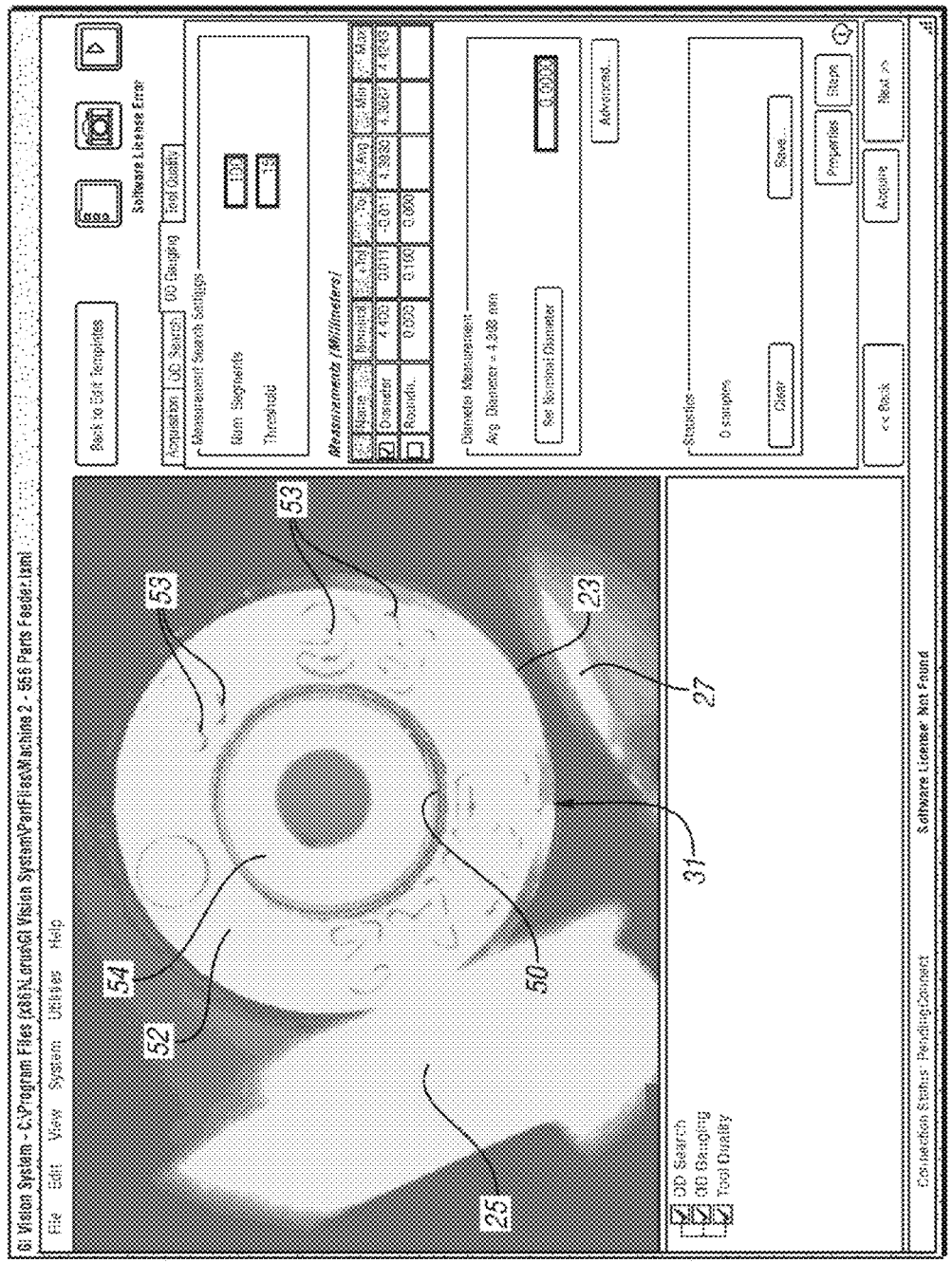
FIG. 8 is a schematic view of a screen shot which shows a primer end of a cartridge case supported between an end wall angled with respect to a conveyor belt for measuring primer pocket diameter.

Initially, parts, such as cartridge cases 31 (FIGS. 4-11), are placed into the hopper of the part transfer subsystem 20. The subsystem 20 is typically controlled by a PLC (FIG. 3) and typically includes a feeder bowl (not shown) having a scalloped rim. The bowl is supported on an adjustable frame structure. Tooling around the rim takes advantage of the asymmetrical mass distribution of the cases 31 to feed the cases 31 onto a feeder conveyor or loader 27. Consequently, every case 31 which exits the bowl is received by the conveyor 27 and is oriented in the same direction as shown in FIGS. 6 and 7. One or more vibrators controlled by a vibrator controller (not shown) may vibrate the bowl. The conveyor 27 moves or conveys the cases 31 in spaced relationship to the primer vision station 22 at which the longitudinal axes of the cases 31 are substantially aligned by the conveyor 27 and a sidewall 25 which together turn a v-shaped moving track (FIGS. 6, 7 and 8).

Figure 18:
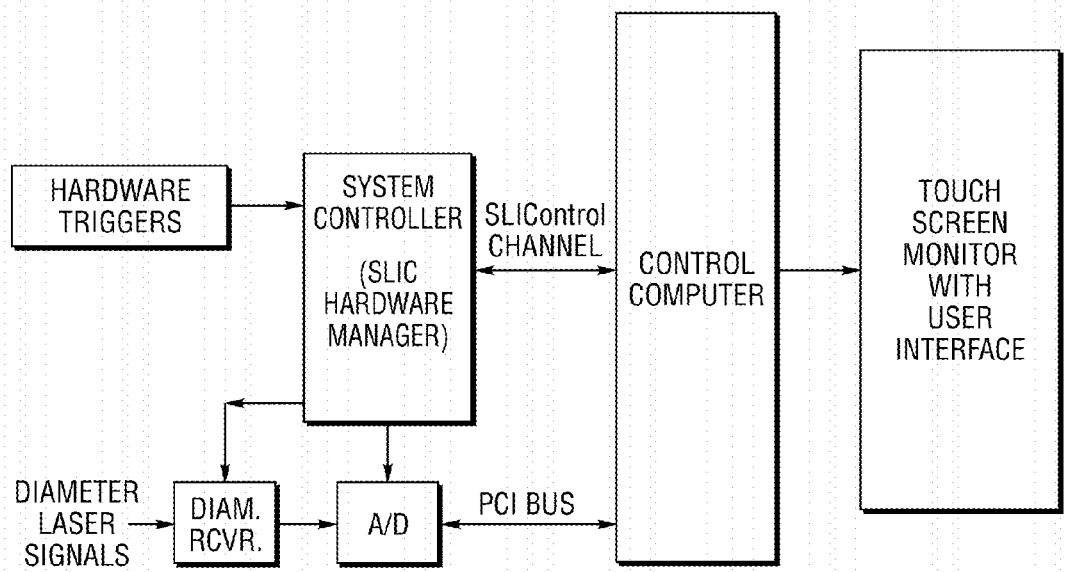
FIG. 18 is a more detailed block diagram of the hardware of FIG. 17.

As the cartridge cases 31 enter the station 22, a laser beam emitted by a laser beam transmitter of U-shaped assembly 19 (FIGS. 6 and 7) is interrupted by each case 31 to provide a trigger signal by a receiver of the assembly 19. The assembly 19 is a hardware trigger, as shown in FIG. 18, which provides a trigger signal to a system controller which, in turn, controls an illumination assembly including an LED ring illumination device 36 (FIG. 4) and a lens and detector assembly including a camera 38. The camera 38 includes a lens or lens subsystem 40 (FIGS. 6 and 7) having an optical axis and a detector such as an image sensor having an image plane at the station 22.

At the vision station 22, each cartridge case axis is aligned with the optical axis of the lens 40 which is preferably a hypercentric or pericentric lens as described in detail below. Consequently, axial or on-axis machine vision viewing is provided. After inspection, the cases 31 are conveyed from the station 22 so that the inspected cases 31 travel along a second path which extends from the station 22. The cases 31 are dropped by the conveyor 27 and the unsupported cases 31 fall onto a v-shaped track 29 where the cases 31 slide under the force of gravity.

The illumination assembly including the device 36 simultaneously illuminates an outer end surface 52 of each case 31 (FIG. 8) and an inner peripheral surface 51 (FIGS. 9 and 10) of a primer pocket 54 (i.e. the annular interior side surface 51 of the pocket 54). The LED ring light 36 (FIGS. 6 and 7) is disposed about the lens 40 at one end thereof and may be an LED ring light made by CCS, Inc. and as generally described in U.S. Pat. No. 8,154,683.

The lens 40 forms an optical image of the illuminated end surface 52 and an optical image of the illuminated inner peripheral surface 51 of the pocket 50 simultaneously on a single image plane of the image sensor to detect the optical images. The end surface 522 may include identifying indicia 53.

The lens 40 preferably is a pericentric or hypercentric lens subsystem 46 wherein the lens subsystem provides a borescopic view of the interior side surface 51 of each primer pocket 50. The surface 51 extends 360° around the pocket 50.

The system 20 also includes a video or image processor in the form of a vision computer (FIG. 4) to process the detected optical images detected by the image sensor to obtain an end view of the case and a 360° borescopic view of the inner peripheral surface 51 of the pocket 50. The detected optical images are processed by the computer or processor to determine a geometric dimension related to the illuminated interior side surface 51 of the pocket 50 such as pocket or primer pocket diameter. In general, a circle is initially found trained on the radius of the inner wall of the primer diameter. The computer fits a best-fit circle to the detected optical image of the inner peripheral surface with between 300-400 points (varies depending on part consistency in appearance, lighting, actual part variation, etc.). Then the computer performs a diameter calculation based on the average of these points.

In particular, the programmed computer extracts edge locations or information along radial lines in the image and then chooses edges which lie on the best circle based on tool settings. An outer search circle is superimposed on the image together with a plurality of search segments to obtain extracted edge locations which represent either Dark-to-Light transitions or Light-to-Dark transitions.

From all edge locations, the algorithm of the computer tries to find the best circle. It does this by iterating through every triplet of points (3 points define a circle), and then counting the number of edges that fall on that circle within some tolerance. Whichever circle has the most edges associated with it is considered to be the best circle.

There are several parameters that can be used to help the algorithm find the correct circle. The simplest is the Edge Polarity, which can eliminate all edges of a certain type in the example image above; since we know that the desired circle should be made up of Dark-to-Light transitions.

Another parameter is the expected radius. If the circle to be found is of a known radius, one can eliminate circles that do not match the expected radius within some tolerance, and this can significantly speed up the algorithm and help eliminate errors.

Once the best circle is located, all of the edge points that were found to fall within tolerance of this circle can be used in a least-squares algorithm to determine an equation for the best-fit circle.

Diameter Measurement

Once the above-noted algorithm has located a circle, the diameter of this circle can be measured. Like the center diameter search, this is done with radial edge finders, and with a rough circle already known. These edge finders can be increased in number and centered on the circle to be measured.

A number of radial edge finder lines (such as 300) can extract edges. The radial lines are centered on the circle located by the above-noted outer diameter search. From this large list of edge locations, the algorithm chooses only those edges which fall within some tolerance of the outer diameter circle. Only up to one edge is chosen for each radial segment.

From the selected list of edge locations, a best-fit circle is determined using a least-squares algorithm. This identifies the center and radius of the circle. Then, each edge location is assigned a diameter equal to twice the distance from the edge location to the center of the circle.

The system also includes a system controller (FIGS. 3-5) which controls and coordinates the inspection and measurement of the cases 31 at the station 22 with the transfer of the cases 31 to and from the station 22 to control movement of the cases 31 and the measurement of the cases 31. The results of the processing by the vision computer are output to the system controller which controls the system based on the results of the optical inspection. The assembly 19 provides various timing or trigger signals to the controller to help control the system. For example, the assembly 19 may signal the controller when the cases 31 are located at or near the vision station 22 in the system so that the lens and detector assembly can be controlled by the controller to take "pictures" of the primer ends 23 of the cases 31 at the vision station 22.

Figure 17:
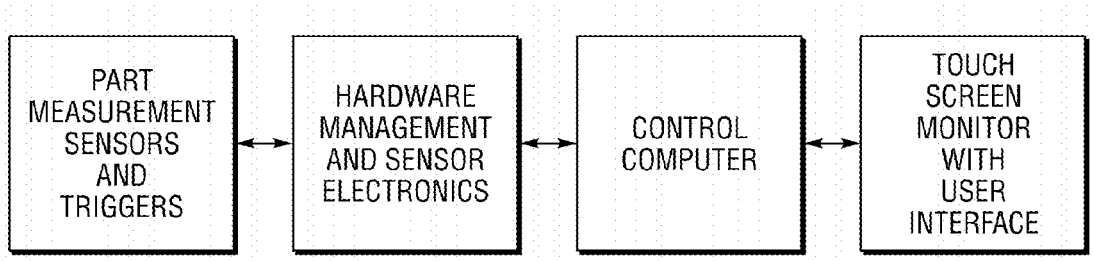
FIG. 17 is a generalized block diagram of hardware constructed in accordance with one embodiment of the system of the present invention.

The system may also include a display or touch screen monitor and a user interface (FIGS. 17 and 18) under control of a control computer (which, in turn, is under control of the system controller) to permit two-way user interaction with the system. The user can define allowable tolerances for each constructed measurement. The software then keeps track of collected data for each part and displays not only the current part's measured dimensions, but also maximum, minimum, median and limited statistical distribution information for each measurement over the duration of the inspection process.

After inspection at the vision station 22, the cases 31 may be dropped onto the track 29 which may take the form of an AMPCO 18 oriented at a 35° angle. As the cases 31 slide down the track 56, they may pass through other inspection stations such as the primer station 26 to be inspected one at a time. Cases 31 which pass each of the inspections may be actively accepted by a part diverter or flipper 32 located at the bottom of the track 29 (FIG. 3). The solenoid-actuated flipper 32 actively accepts those parts which have passed every one of the above tests. This flipper 32 rests by default in the reject position so that parts will not be falsely accepted in the unlikely event of a hardware or software malfunction.

Figure 5:
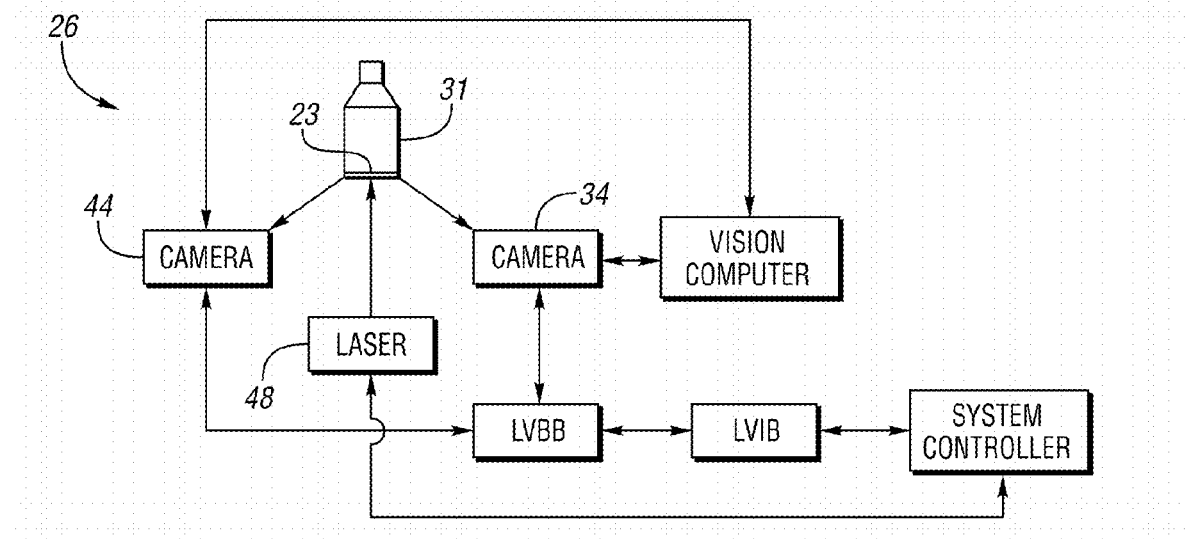
FIG. 5 is a detailed schematic view of hardware located at a primer depth station of the inspection stations and their control.
Figure 11:
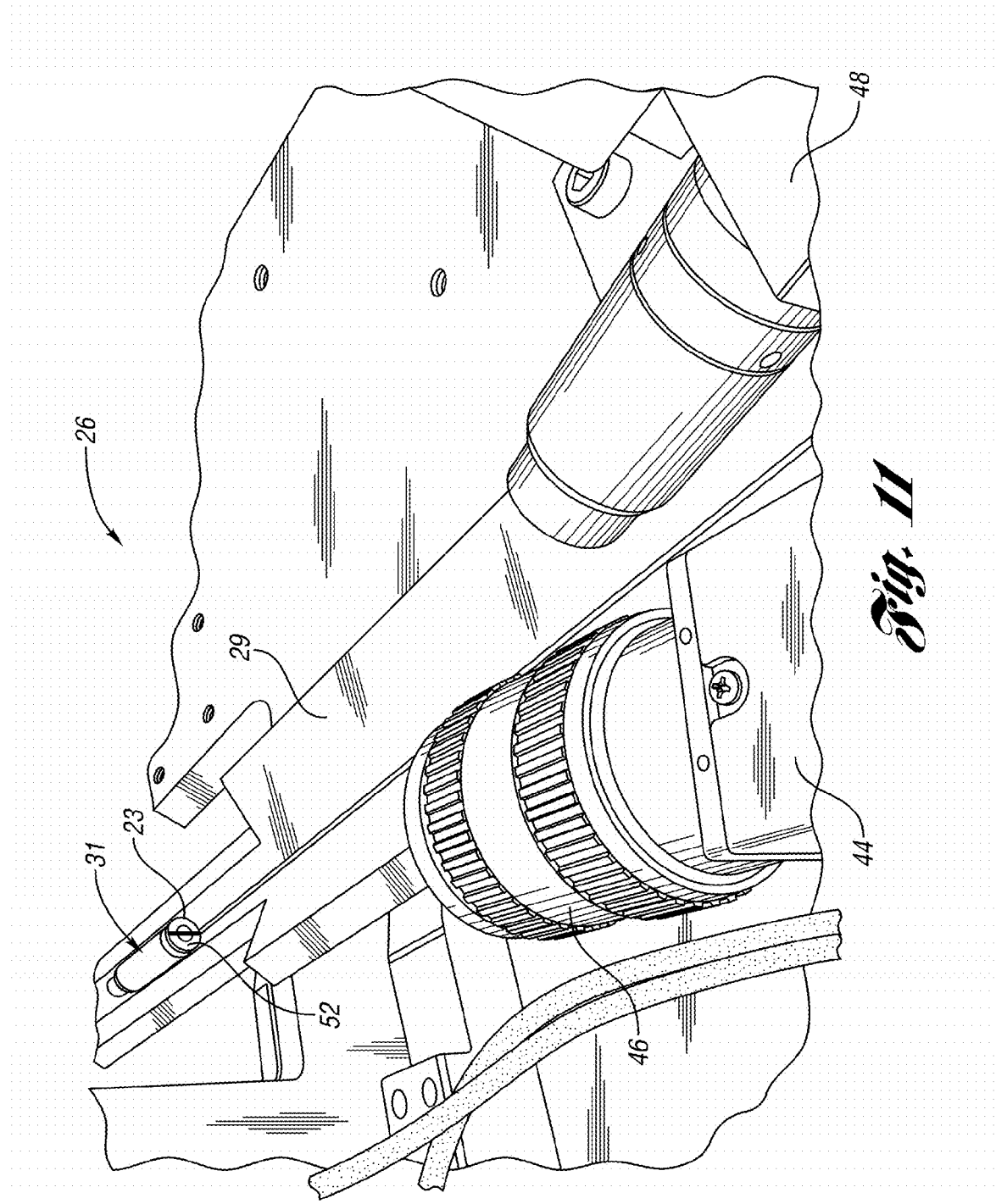
FIG. 11 is a perspective schematic view, partially broken away, of the hardware located at the primer depth station of FIG. 5 but with a single camera.
Figure 12:
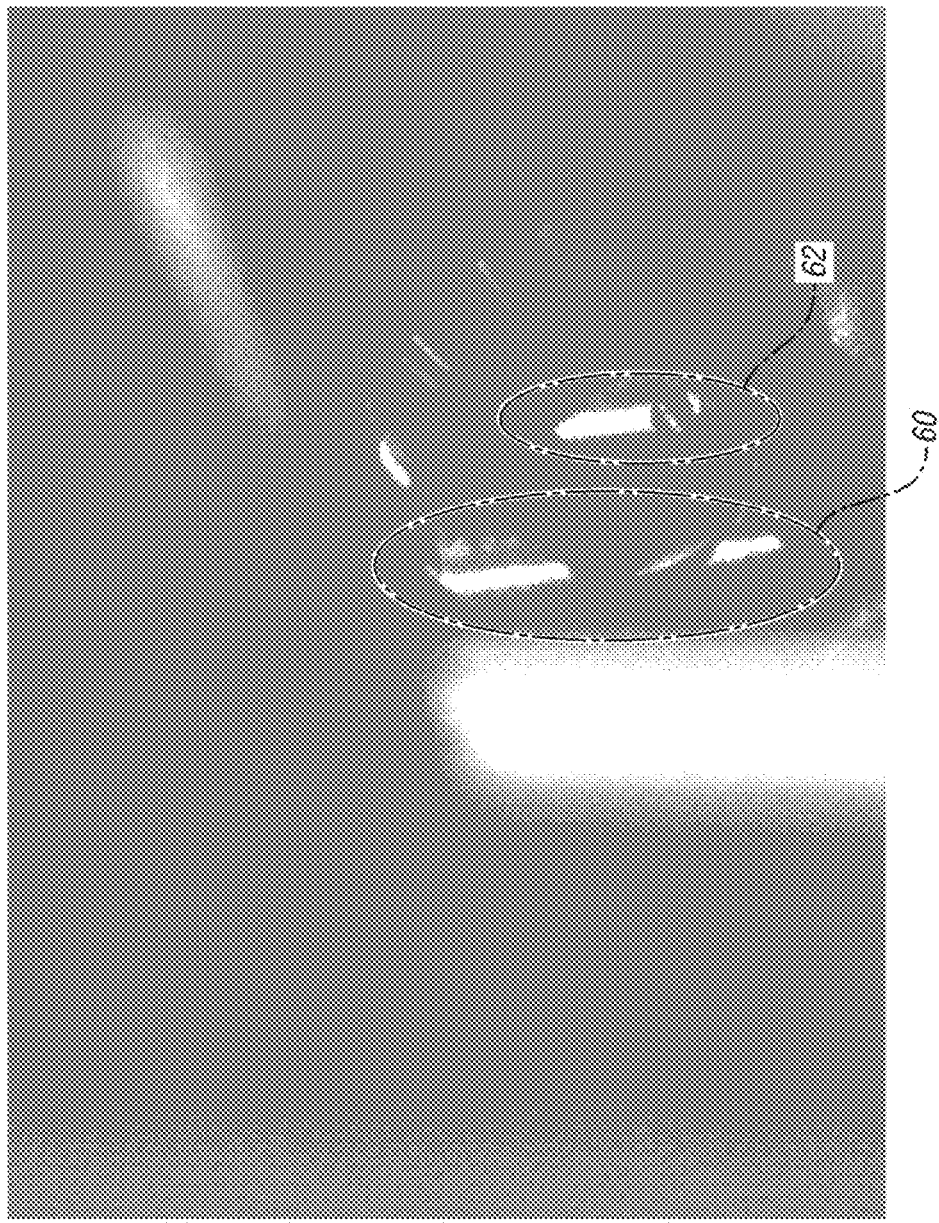
FIG. 12 is a schematic view an optical image of portions or segments of a laser line reflected from an external end surface and an internal end surface of a cartridge case.
Figure 13:
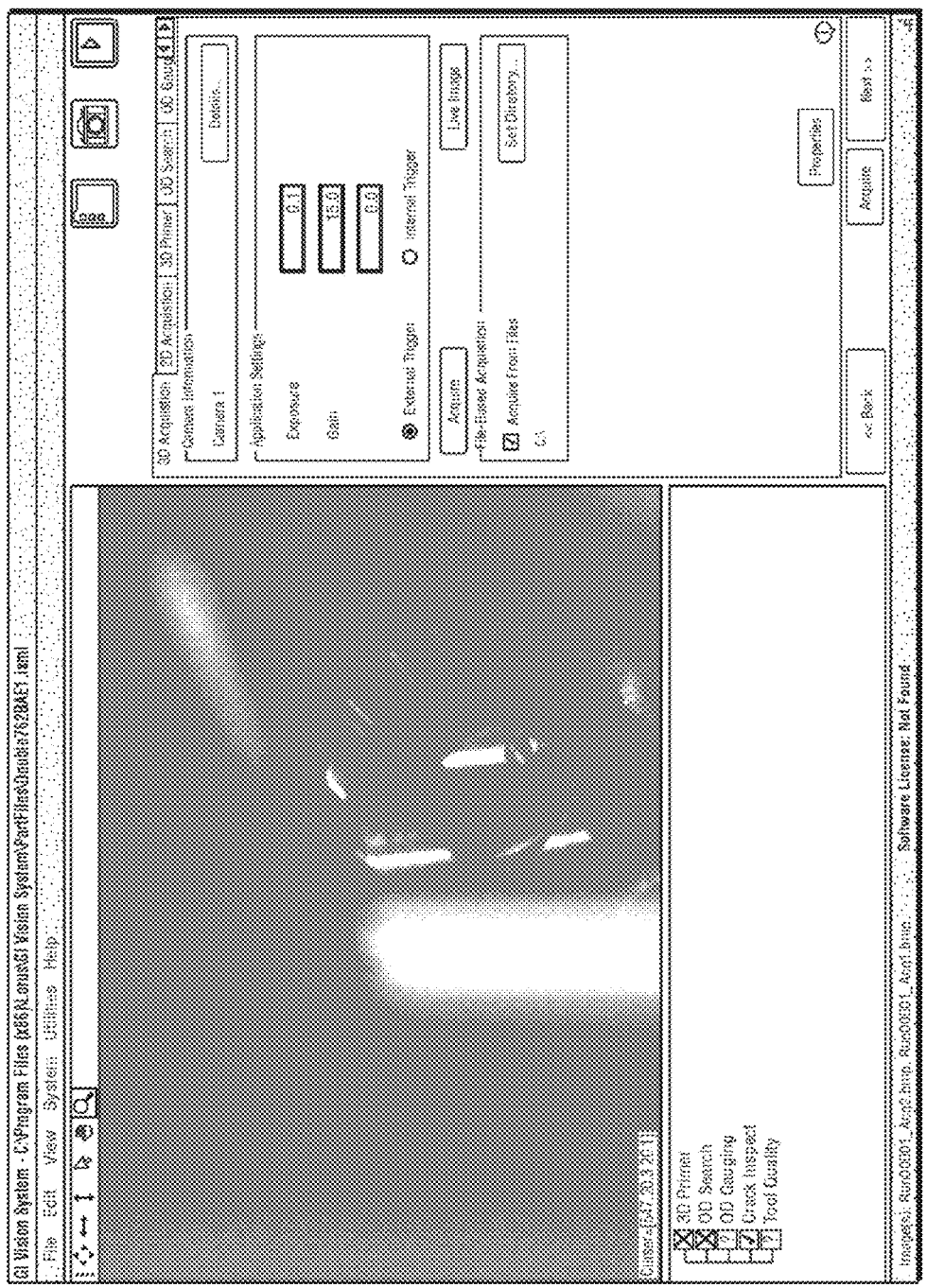
FIG. 13 is a schematic view of a screenshot which shows camera exposure time and gain for image acquisition by a first camera.

Referring now to FIGS. 5 and 11, at the primer depth station 26, pencil light beams in the V-slide or track 29 monitor the part's progress as it slides down on the inclined, upper surface of the track 29. Each pencil light beam is associated with a small control unit or hardware trigger that produces an electrical pulse when the light is blocked. The pulse is referred to as a "trigger." Also, at the primer depth station 26, a projector in the form of a line-generating laser 48 disposed above the track 29 project a visible line of laser radiation having a vertical orientation onto the exterior and interior end surfaces 52 and 54, respectively, of the case 31 to obtain line segments of laser radiation 60 and 62, respectively, (FIG. 12) reflected from the end surfaces 52 and 54.

At least one (as shown at 44 and 46 in FIG. 11) and preferably two (as shown at 34 and 44 in FIG. 5) cameras or lens and detector assemblies form optical images of the reflected line segments of laser radiation (60 and 62 in FIG. 12) and detect the optical images to obtain electrical signals. One assembly includes the camera 44 having a lens 46 (FIG. 11) and the other assembly includes a camera 34 having a lens (not shown in FIG. 5). The pair of lens and detector assemblies (FIG. 5) are disposed on opposite sides of the path that the case 31 takes along the track 29 to form the optical images of the reflected line segments of laser radiation and to detect the optical images to obtain the electrical signals. Each detector or camera 34 or 44 includes an image sensor having an image plane to detect the optical images.

A processor typically in the form of a vision computer processes the electrical signals to determine a geometric dimension which, in this embodiment, is primer pocket depth.

Figure 16:
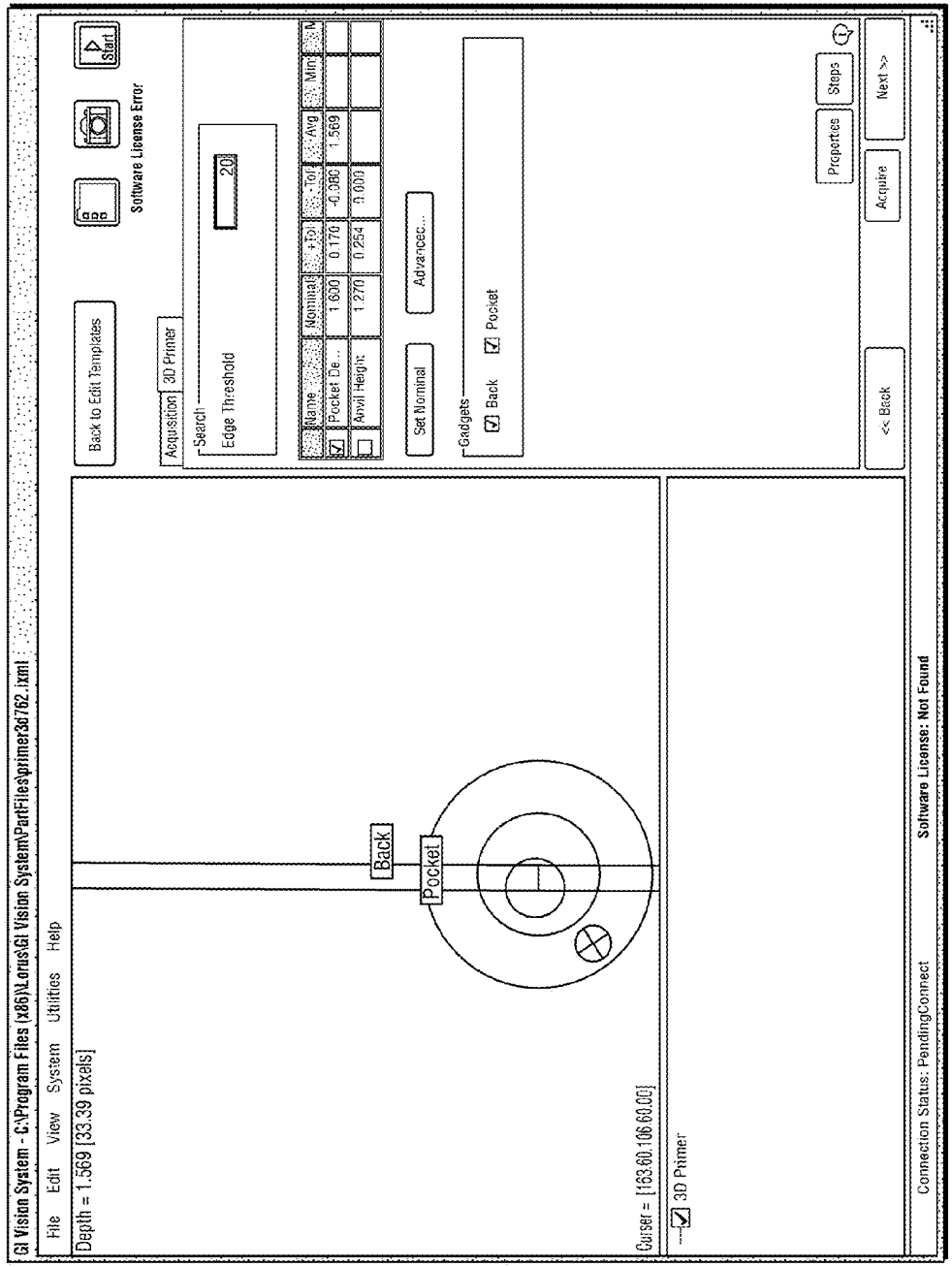
FIG. 16 is a schematic view of a screen shot which shows the measurement of primer pocket depth as the perpendicular distance between two fitted lines.

Referring to FIGS. 5, 11, 12 and 16, the ultra-thin line generating laser 48 projects a vertical line across the head/primer bottom 23 of the part 31. The two cameras 34 and 44 at opposing angles see this projected line on the exterior end surface 52 of the head 23 and a distance away (FIG. 12) at the interior end surface 54 of the primer pocket 50. Both of the cameras 34 and 44 see the line segment at the base or interior end surface 54 of the primer pocket 50. An algorithm finds the center of a laser line which fits a line to each laser line segment and then performs a distance calculation between the two line segments as shown in FIG. 16.

In particular, laser triangulation is used to locate the primer pocket depth. The laser line generator has its line focused onto the primer of the part. Two cameras, on opposing sides of the laser line generator, are used to triangulate the depth of the primer pocket. Triangulation is a well-known technique to extract 3-D information from a 2-D image.

Figure 14:
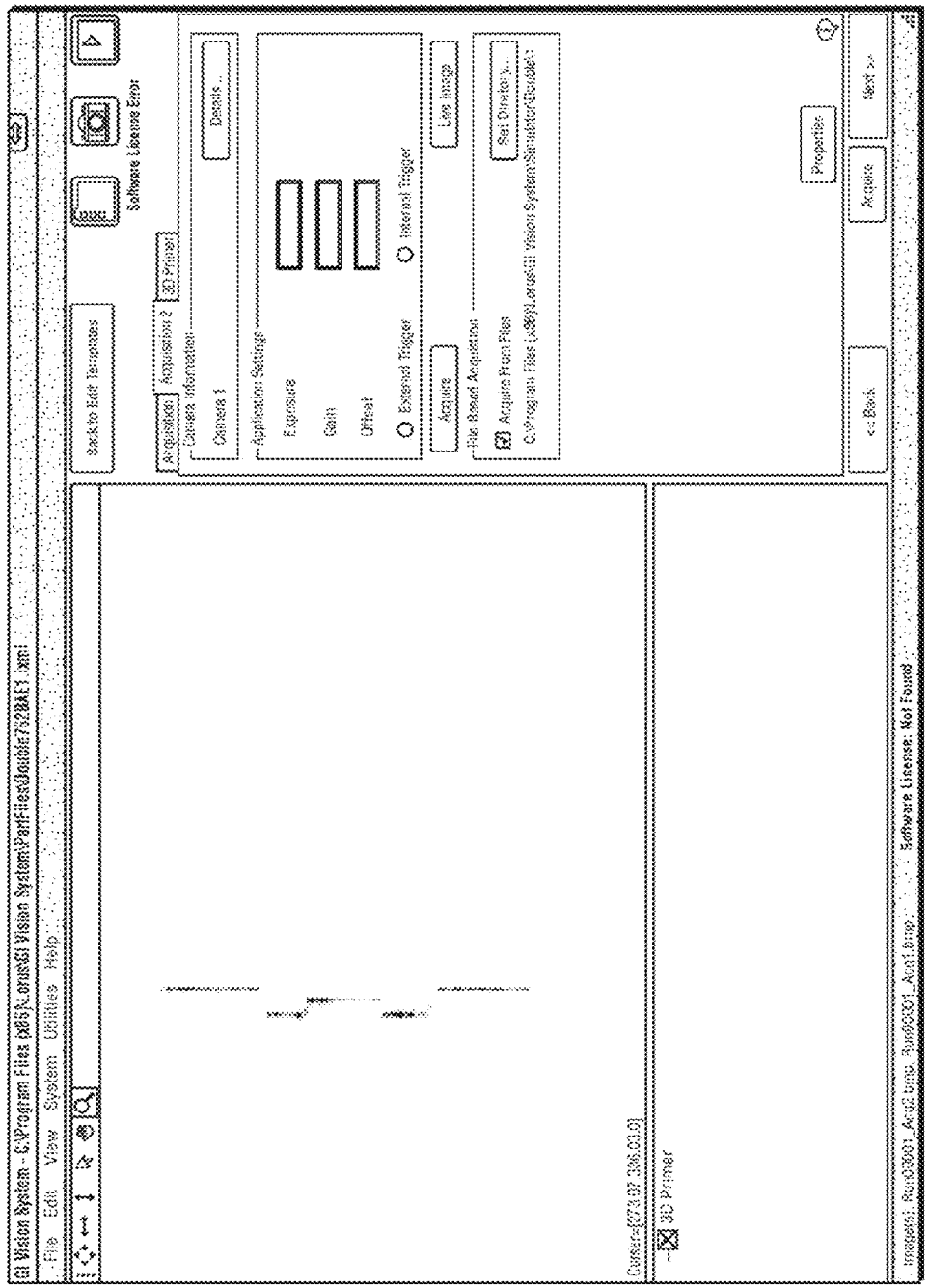
FIG. 14 is a view similar to the view of FIG. 13 for a second camera.
Figure 15:
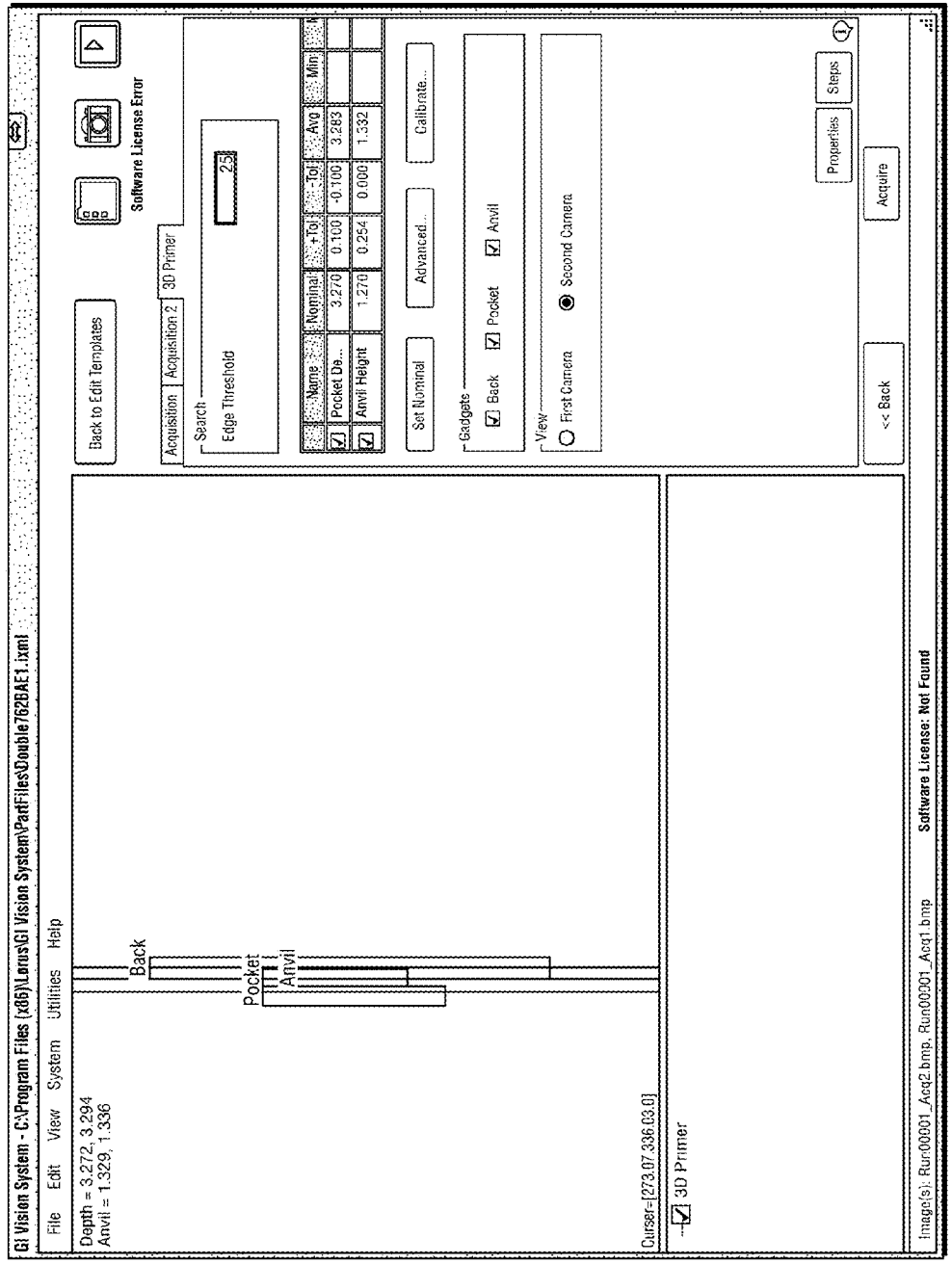
FIG. 15 is a schematic view of a screenshot which shows 3-D primer depth measurement using a second camera.

The image shown in FIG. 14 is from one of the cameras. The leftmost pair of lines are the bottom of the primer pocket, the center line is from the anvil (which is not present on all parts) and the two longest lines on the right side are from the back side of the part.

A Primer Pocket Depth algorithm locates each of these lines. The algorithm gives the user a window to surround each of these sets of lines. The tool then extracts edge information from the image and attempts to create the line equation for each line (or pair of lines) at each of the three different depths.

The algorithm gives several options to make measurement more accurate. When edges are extracted, the tool can select edges on the left side of the line, the right side, or both (in which case the left and right edges are averaged together to find a point near the center of the line). This can be useful if, for whatever reason, one side of the line has better edge information than the other.

Another option the algorithm presents is the ability to use the slope of the longest line (the back of the part) as the slope on the other 1 or 2 lines. When selected, this option assumes a priori knowledge that the anvil and the bottom of the pocket should be parallel to the back of the part, and this can help make measurements more repeatable.

Line finding for this algorithm is done in two steps, a rough locate and a fine locate. For the rough locate, edges are extracted at larger intervals, for example, we might find edges at every $10^{th}$ row in the window. Once a set of edges is found, the rough locate algorithm attempts to locate the best line to fit these edges. This is done by taking every possible pair of edges, creating a line between them, and then counting the total number of edges that fall on this line (or near enough to be considered "on" the line).

The "best" line is the one that has the most edge points that fell on or near that line. If two lines have the same number of edge points, then the best one is whichever line has the smallest sum of distances between the line and the edge points that were chosen for that line.

After choosing a best line, the edge points that were considered on or close to that line are all used in a least-squares fit to determine the final equation of the rough line.

The second step in the algorithm is the fine locate of the line. It extracts edges at smaller intervals in the window. For example, it might do it on every row of the window. Once all the edges are found, those that are too far from the rough line, based on some adjustable tolerance, are discarded. The resulting edges are put through a least-squares fit to find the final line equation.

System Logic

Figure 4:
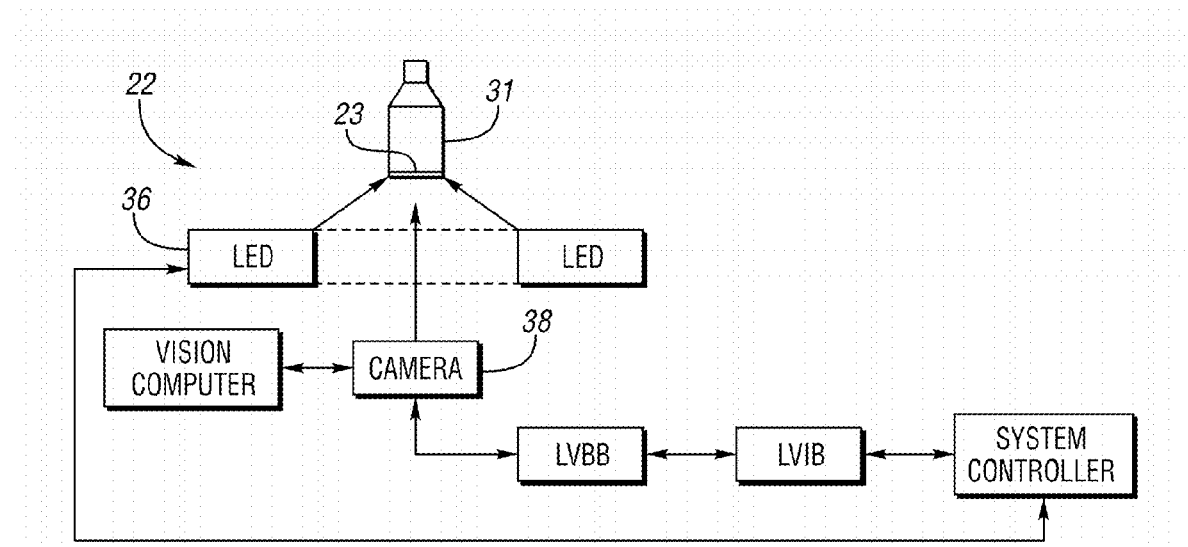
FIG. 4 is a detailed schematic view of hardware located at a primer vision station of the inspection stations and their control.

Referring to FIGS. 3, 4 and 5, the system logic includes a System Logic Interface Controller (SLIC) or system controller. This controller takes "PART RESULT" and "PART COMPLETE" inputs from all of the inspection stations in the system. The SLIC communicates directly with a Uni-Flipper Interface Board (UFIB) and instructs the flipper 32 to actively accept parts into a part receive area 33 for which it has received positive part result and part complete signals from each inspection station. Each inspection station must have reported a positive part and part complete signal for the SLIC to instruct the UFIB to open the flipper 32 (as illustrated in FIG. 3) through the solenoid. Otherwise, the defective parts fall to a defective part area 35.

Images taken by the vision cameras 38, 34 and 44 located above or adjacent the vee-track 29 are preferably processed by dedicated vision computers as previously described. Once the vision computers have performed the user-defined tests and measurements they communicate back to their respective cameras, the geometric dimensions and whether or not the measurements were outside a range of acceptable values (i.e. are defective).

Referring again to FIGS. 17 and 18, the hardware for the stations of the system include a number of subsystems. Part measurement sensors and triggers include cameras as sensors, and hardware triggers that monitor the passage of the parts. Hardware management and sensor electronics include the system controller in the form of the SLIC hardware manager and a number of modules required to convert the measurement signals to information the control computer can utilize. The control computer performs signal processing and manages the user interface at a monitor or monitor display.

Figure 19:
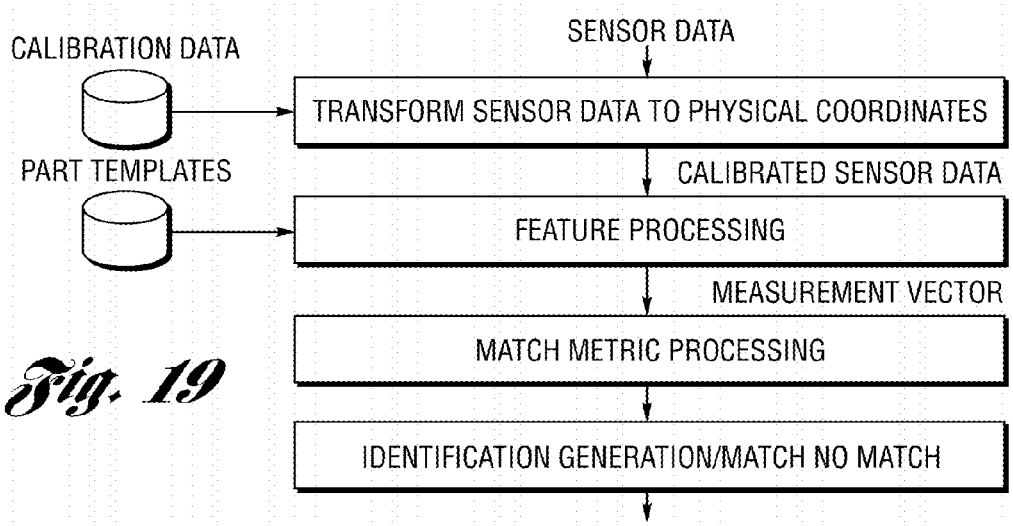
FIG. 19 is a block diagram which illustrates the flow of data utilizing one embodiment of a method of the present invention.

Referring now to FIG. 19, the data and signal processing steps described therein illustrates how the system processes sensor data and identifies and measures a part presented to the system. Using calibration data, sensor data is transformed to a description of the part, specified in calibrated physical coordinates. Feature processing extracts values for each feature contained in the entire part template data set. Match metric processing identifies the best match to the sensor data among the part templates. Identification generation evaluates the best match; if the match is good enough, the part is said to be identified, otherwise the part is not identified.

In general, when setting up a new part, the user chooses "features" of the part to be measured. For most features, the user chooses a region of the part where the measurement will be made, a nominal value of the measurement, and plus and minus tolerances. For some features, the measurement region may be the whole part.

More particularly, in creating a template, a gold or master part such as a cartridge case with known good dimensions is conveyed by the conveyor 27 and then dropped on the inclined track 29 so it slides down the track 29 after the particular part is named. After the part has traveled the length of the track 29, an image of the part is displayed on the screen or monitor.

Appendix

Figure 9:
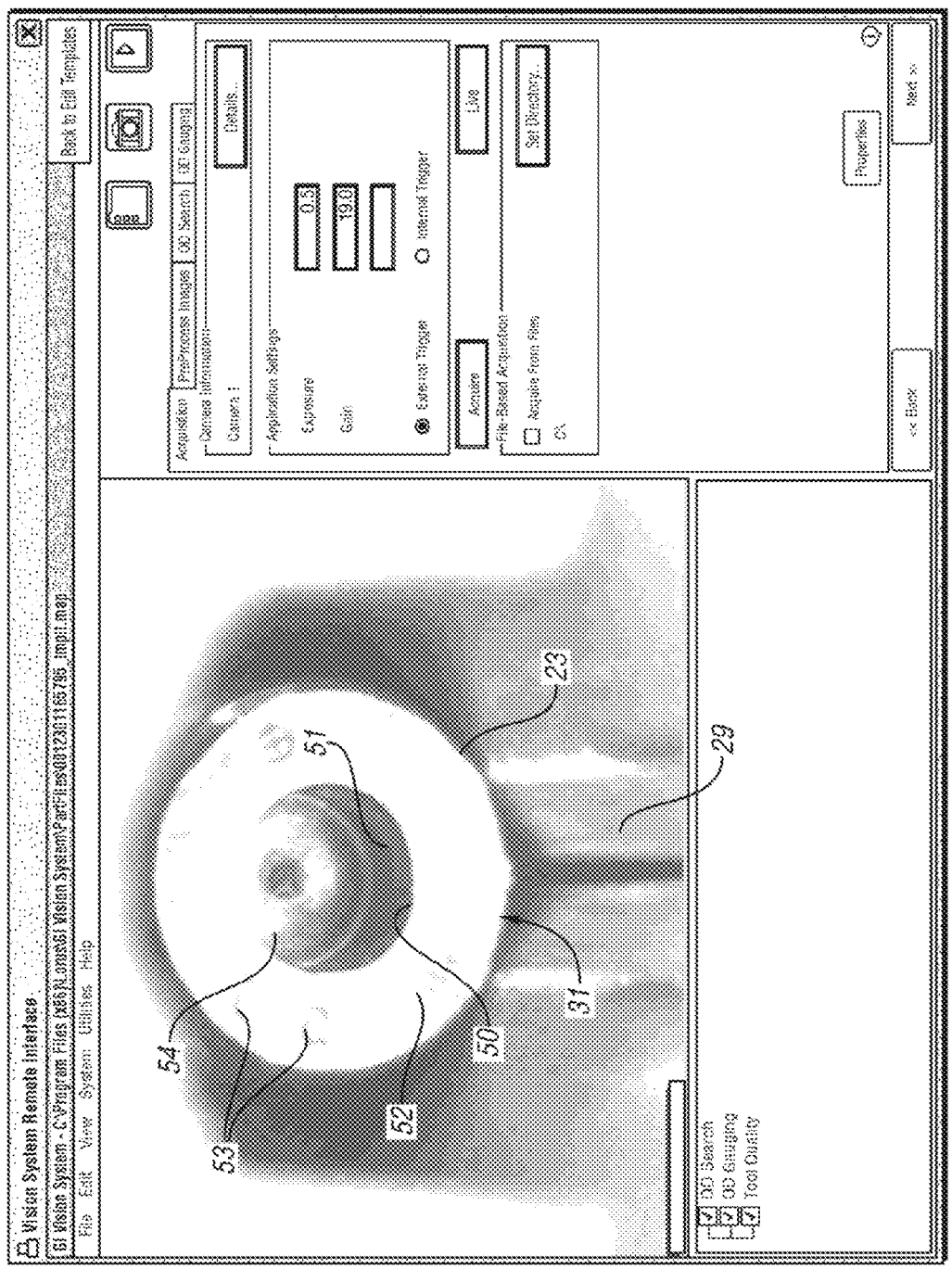
FIG. 9 is a schematic view of a screen shot which shows a primer end of a cartridge case supported on a V-shaped track and which allows one to adjust camera exposure time and gain.
Figure 10:
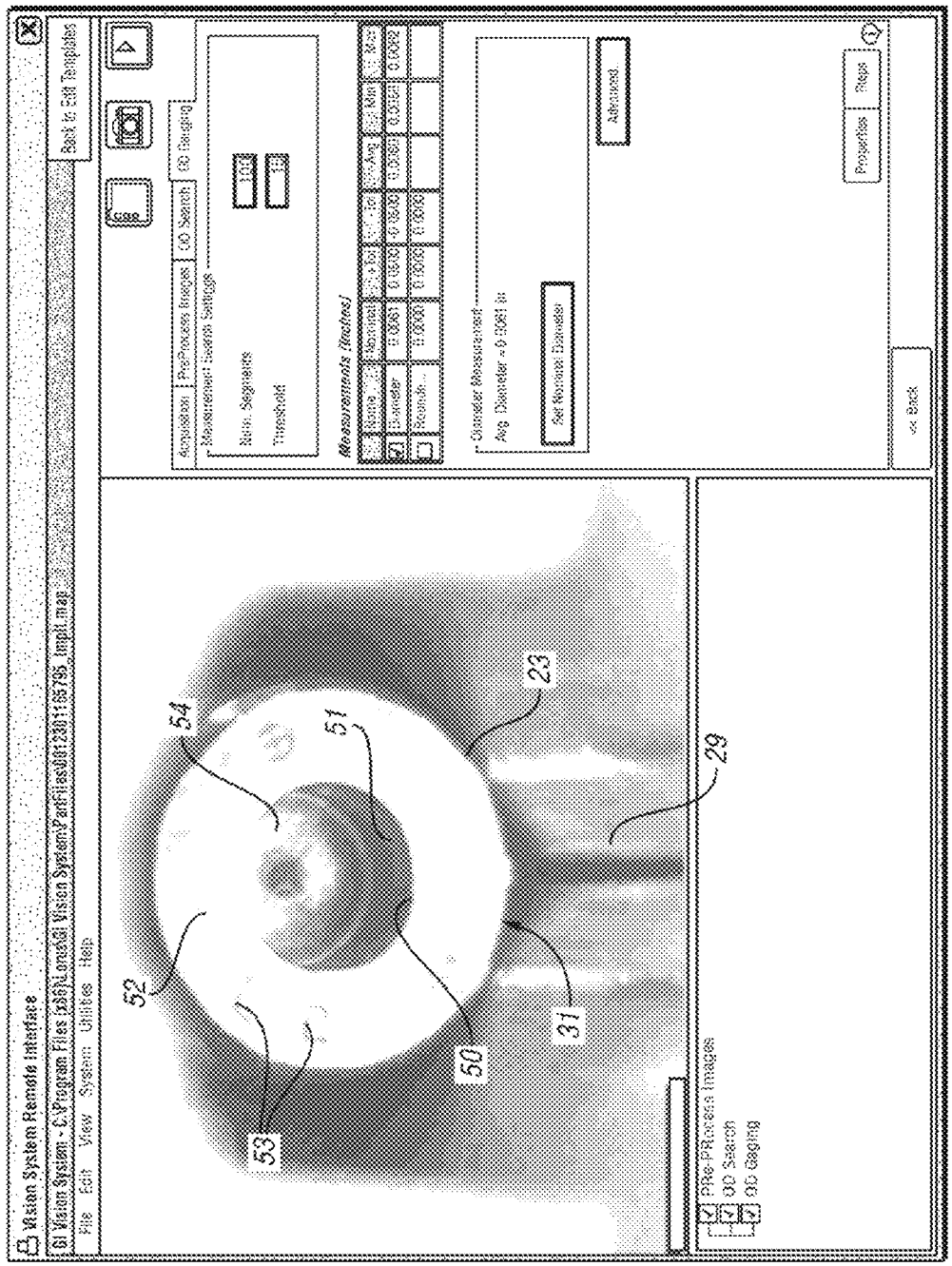
FIG. 10 is a schematic view similar to the view of FIG. 9 which allows one to check for pocket roundness and measure the diameter of the pocket.

Referring now to FIGS. 9 and 10, schematic views of screen shots are utilized in combination with the following description for primer vision setup.

1.1.1 The standard vision setup is for the vision option that can be added to most any sorting machine.

1.1.2 Aligning the equipment:

1. Aligning the equipment as previously described.

1.1.3 Camera Settings

1. On the main vision screen, make sure that the camera settings button is selected. From here you will need to adjust the camera's exposure time and gain. Also, on the camera itself, you will need to adjust the focus and F-Stop to get the proper image needed for inspection.

2. Once you have the camera height and lighting adjusted for the part that is being setup, the camera's focus, F-Stop, exposure time, and gain will need to be adjusted.

3. First you will need to set the F-Stop on the camera and the gain from within the software. This will set the brightness for the part.

a. The F-Stop is the adjustment on the camera closest to the base of the camera. Adjusting the F-Stop allows either more or less light into the camera, depending on which direction the adjustment is made.

b. The gain will make the image darker for lower settings and brighter for the higher settings. After you have obtained the desired brightness on the part, you will need to focus the camera to get the best image possible.

c. The focus is the closest adjustment to the lens. You will have to turn this until the part becomes focused on the screen. You can start off in live mode, but it will need to be tested with the external trigger set, so you can see how it passes through the camera while parts are passing through the camera.

4. Within the camera settings screen, there are a few adjustments that can be made. There is a trigger option. This lets you choose between an internal or external trigger.

a. Internal trigger is set to take continuous images when the camera is in play made.

b. External trigger will only take pictures in play mode when a part passes through the trigger.

5. The camera's exposure time and gain can also be adjusted from this screen.

a. Exposure time is the camera's shutter speed. The lower the shutter speed, the faster the camera will take the image. It should be set around 0.2 ms to 2.0 ms. If part seems blurred while passing through the camera, then the exposure time should be lowered.

b. The Gain helps brighten or darken the image. If the gain is set too high, it will allow more noise into the image. The F-Stop on the camera should be used in conjunction with the gain to acquire the proper brightness for each of the parts.

c. Different lenses will be required for various part sizes.

1.1.4 Setup Screen Settings.

1. The following options can be added for inspection in any combination within the vision system:

b. Pre process—This tool is used to correct any distortion caused by the angle of the camera;

c. OD Search—This tool locates the outside diameter of the head.

d. Crack Inspect—This tool sets up the parameters for looking for the defects on the edges of the mouth. This tool is used for large and small cracks (multiple inspections can be setup).

OD gauging—This tool can be setup to inspect the diameter of the primer pocket.

A comprehensive crack inspection setup may require the use of multiple crack inspection tools. The primer Gauging step can detect extremely large cracks, the crack inspect can find other large cracks and find small cracks. It is unrealistic to just use one crack inspect to find all cracks because, for example, it has specifically been setup to locate small cracks. Extensive research into crack detection has shown that this type of multi-algorithm approach is the best way to locate defective parts.

2. To select which features will be enabled for the part you are setting up, select "Edit device" from the top tool bar. A drop down menu will appear; select "Device" from the menu and a screen will appear.

Checking the box in front of the feature will enable that feature for inspection. If a features is not needed for that sort, un-check it and the feature will not be checked for the part setup. One only needs to select the features that are appropriate for the defects one is checking for. One may select and setup for all of the features, but this may result in more good parts getting rejected unnecessarily.

1.1.5 OD Search

1. Only a few things need to be adjusted when setting up for OD search.

a. Num. Segments—this determines how many different diameters will be used to find the outer edge of the OD b. Dark to light—This option is set to look for dark pixels on the part with a bright background.

c. Light to dark—This option is set to look for bright pixels on the part with a dark background.

OD Threshold—The threshold can be either raised or lowered to help locate the outside edge of the part.

After selecting either the Bright or Dark circle, one can adjust the edge threshold. Edge Threshold is used to help find the edge of the parts. By dragging the edges of a circle (located every 90 degrees), one can either make it larger or smaller. The circle should be at least 10% bigger than the head of the part. Lines are what find the edge of the part as they cross a different circle. After aligning the first circle, adjusting the edge threshold will allow for more of the lines to find the second circle. Where the lines find the second circle, one sees a spot, this is where it is finding the edge. Once one finds the edge of the head, pass a part through the camera with the external trigger on and check to make sure the OD search tool is finding the part every time. If the outside of the part is not found every time, make more adjustments until the part is found every time.

1.1.6 OD Gauging

1. Under the OD gauging tab, one can check for the pocket roundness and measure the diameter:

d. Search Settings—In this area one can adjust the settings for the boxes that are looking for the outer diameter and edge of the part. Always set this up on a good part. The tool is referenced off the OD search, which should already be setup. One can change the threshold and the number of segments that are being used.

e. Threshold—The threshold can be either raised or lowered to help locate the outside edge of the part.

f. Num Segments—Increasing or decreasing the number of segments will either add or subtract the number of boxes looking at the diameter. Increasing the number of segments may help in finding smaller roundness defects.

g. Outer Diameter—The Outer diameter inspection area is designed to inspect the diameter measurement in pixels. After setting up the search area on a good part, one can look in the diameter area and press the set nominal button. This will place the actual into the nominal position for the part. Once the nominal is set, one can adjust plus and minus tolerances accordingly.

2. Calibrating the OD gauge—OD gauging can also be set up to measure in actual measurements instead of pixels. This is done the same way as it is for mouth gauging.

Referring now to FIGS. 11-16, schematic views of screen shots are utilized with the following description for 3-D primer vision.

3-D Primer vision consists of two parts, the laser, and the camera(s).

The laser line crosses the head and the primer pocket.

The camera(s) must be set to be able to see both the laser line segments on the head and the laser line segment in the pocket.

3-D primer vision allows for the checking of primer depth. The 3-D primer vision software consists of 2 parts, acquisition and measurement.

Acquisition

Acquisition is almost identical to all other vision acquisitions, with the exception of needing a lower level of light to allow a better view of the laser line segments. If one has a 2 camera depth system, one will have 2 acquisition tabs, one for each camera. The lighting adjustments are best done with the F-stop of the camera. Using the digital gain has lower limitations that the F-stop does not.

The measurement feature works by measuring the distance between where a laser lands on the outside surface of the head and where it lands on the inside surface of the primer pocket (or anvil).

1. Slide a good part or your golden part/gauge down the track

2. Set the "back" box around the "back" end where the laser crosses on the head

3. Set the "pocket" box around the area where the laser crosses the bottom of the pocket 4. If one has an anvil, set the "anvil" box around where the line crosses over the tip. If one measures the anvil as the distance from the edge of the head to the tip, click "advanced" and select "measure depth" on the anvil setting. If anvil is from the anvil tip to the bottom, make sure it is unchecked 5. Measure the depth of the primer pocket and anvil for the piece you are setting up with, click on the "calibrate" button and enter these values in and press ok Enter in the nominal depth and tolerances If the system has 2 cameras one will see the option under "view" for first or second camera, make sure both are setup as above. Do this before calibrating to the known value.

Certain implementations of the invention comprise computer processors which execute software instructions which cause the processors to perform at least one step of an algorithm or method of at least one embodiment of the invention. For example, one or more data processors may implement the methods described herein by executing software instructions in a program memory accessible to the processors. At least one embodiment of the invention may also be partially provided in the form of a program product. The program product may comprise any medium which carries a set of computer-readable signals comprising instructions which, when executed by a data processor, cause the data processor to execute at least one step of the method.

Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, EPROMS, flash RAM, or the like. The software instructions may be encrypted or compressed on the medium.

Where a component (e.g., software, a processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A high-speed, 3-D method of optically measuring a geometric dimension of a plurality of manufactured parts, the method comprising:

consecutively transferring the parts so that the parts travel along a path which extends to a vision station at which each of the parts has a predetermined position and orientation for optical measuring, each of the parts having an exterior end surface and an interior end surface at a first end of each of the parts, the first end of each of the parts having a length and a width, each of the parts having a part-holding pocket extending from the exterior end surface to the interior end surface, the part-holding pocket having a depth defined between the exterior end surface and the interior end surface;

projecting a line of radiation having a predetermined orientation onto the end surfaces to obtain reflected line segments of radiation from the end surfaces of the part;

detecting the reflected line segments of radiation at one or more image planes to obtain electrical signals; and processing the electrical signals utilizing a depth algorithm to determine the depth of the part-holding pocket between the exterior end surface and the interior end surface.

2. The method as claimed in claim 1, wherein the part includes a cartridge case, wherein the first end is a primer end and wherein the part further includes a mouth end opposing the primer end, wherein the exterior end surface and the interior end surface are located at the primer end and wherein the part-holding pocket is a primer pocket.

3. The method as claimed in claim 2, wherein the end surfaces are substantially parallel to each other and wherein the geometric dimension is primer depth.

4. The method as claimed in claim 3, further comprising comparing the primer depth to a range of acceptable depth values.

5. The method as claimed in claim 4, further comprising generating a signal based on the comparing and indicating a result of the comparing.

6. The method as claimed in claim 1, further comprising:
providing an inclined track to support the part along the path; and
allowing the part to fall freely onto the inclined track so that the part slides down the track by the force of gravity.

7. The method as claimed in claim 1, wherein each part has a part axis defined as being central to the part and parallel to its length.

8. The method as claimed in claim 1, further comprising coordinating the measuring of the parts at the vision station with the transfer of the parts to and from the vision station to control movement of the parts and the measuring of the parts.

9. The method as claimed in claim 1, wherein the line of radiation is a line of laser radiation.

10. The method as claimed in claim 1, wherein the reflected line segments of radiation are detected in a pair of image planes.

11. A high-speed, 3-D system for optically measuring a geometric dimension of a plurality of manufactured parts, the system comprising:

a part transfer subsystem including a transfer mechanism adapted to consecutively transfer the parts so that each of the parts travel along a path which extends to a vision station at which each of the parts has a predetermined position and orientation for optical measuring and to transfer each of the parts after measuring at the vision station so that the parts travel along the path which extends from the vision station, each of the parts having an exterior end surface and an interior end surface at a first end of the part, the first end of each of the parts having a length and a width, each of the parts having a part-holding pocket extending from the exterior end surface to the interior end surface, the part-holding pocket having a depth defined between the exterior end surface and the interior end surface;

a projector to project a line of radiation having a predetermined orientation onto the end surfaces to obtain reflected line segments of radiation from the end surfaces;

at least one lens and detector assembly to form optical images of the reflected line segments of radiation and to detect the optical images to obtain electrical signals; and a processor to process the electrical signals utilizing a depth algorithm to determine the depth of the part-holding pocket between the exterior end surface and the interior end surface.

12. The system as claimed in claim 11, wherein the part includes a cartridge case, wherein the first end is a primer end and wherein the part further includes a mouth end opposing the primer end, wherein the exterior end surface and the interior end surface is located at the primer end and wherein the part-holding pocket is a primer pocket.

13. The system as claimed in claim 12, wherein the end surfaces are substantially parallel to each other and wherein the depth is a primer depth.

14. The system as claimed in claim 13, further comprising a computer to compare whether the depth is within a range of acceptable values and to generate a signal based on and indicating the result of the comparison.

15. The system as claimed in claim 11, wherein the system includes a pair of lens and detector assemblies disposed on opposite sides of the path to form the optical images of the reflected line segments of radiation and to detect the optical images to obtain the electrical signals.

16. The system as claimed in claim 11, wherein each part has a part axis defined as being central to the part and parallel to its length.

17. The system as claimed in claim 11, wherein each detector includes an image sensor having an image plane to detect the optical images.

18. The system as claimed in claim 11, wherein the transfer mechanism includes an inclined track to support the part as the part slides down the track by the force of gravity along the path.

19. The system as claimed in claim 11, wherein the projector includes a line-generating laser disposed above the path.

20. The system as claimed in claim 19, wherein the laser generates a visible vertical line of laser radiation.

\* \* \* \* \*